(12) United States Patent
Bernstein

(10) Patent No.: US 9,465,047 B2
(45) Date of Patent: Oct. 11, 2016

(54) MEMS DOSIMETER

(75) Inventor: Jonathan J. Bernstein, Medfield, MA (US)

(73) Assignee: THE CHARLES STARK DRAPER LABORATORY, INC., Cambridge, MA (US)

(*) Notice: Subject to any disclaimer, the term of this patent is extended or adjusted under 35 U.S.C. 154(b) by 705 days.

(21) Appl. No.: 13/563,245

(22) Filed: Jul. 31, 2012

(65) Prior Publication Data

US 2012/0297871 A1    Nov. 29, 2012

Related U.S. Application Data

(62) Division of application No. 12/613,446, filed on Nov. 5, 2009, now Pat. No. 8,258,799.

(60) Provisional application No. 61/112,563, filed on Nov. 7, 2008.

(51) Int. Cl.
| | | |
|---|---|---|
| G01R 27/08 | (2006.01) |
| G01R 31/08 | (2006.01) |
| G01P 15/12 | (2006.01) |
| G01P 15/135 | (2006.01) |
| G01P 15/00 | (2006.01) |
| G01N 27/04 | (2006.01) |
| F41H 1/02 | (2006.01) |

(Continued)

(52) U.S. Cl.
CPC .............. *G01P 15/135* (2013.01); *F41H 1/02* (2013.01); *F41H 1/04* (2013.01); *F42D 5/00* (2013.01); *F42D 5/04* (2013.01); *G01L 5/14* (2013.01); *G01L 9/0042* (2013.01); *G01L 15/00* (2013.01); *G01N 27/04* (2013.01); *G01P 15/00* (2013.01); *H01H 1/0036* (2013.01); *H01H 35/146* (2013.01); *H01H 35/2657* (2013.01); *A61B 2562/028* (2013.01)

(58) Field of Classification Search
CPC ...... G01P 1/023; G01P 15/135; G01P 15/00; G01P 15/12; B81B 2201/0235; G01N 27/04
USPC ..................... 324/691, 525; 73/862, 514.33
See application file for complete search history.

(56) References Cited

U.S. PATENT DOCUMENTS

| 3,341,797 A | 9/1967 | Watson |
| 3,638,160 A | 1/1972 | Huddleston |

(Continued)

FOREIGN PATENT DOCUMENTS

| JP | 07-089124 B | 9/1995 |
| SU | 669234 A1 | 6/1979 |

OTHER PUBLICATIONS

"Unit VI: Explosive Blast" [online] Slide Show for FEMA E155—Building Design for Homeland Security Course, U.S. Department of Homeland Security, Federal Emergency Management Agency, Jan. 2004, Retrieved from the Internet: <http://www.fema.gov/pdf/plan/prevent/rms/155/e155_unit_vi.pdf>, 28 pages.

(Continued)

*Primary Examiner* — Amy He
(74) *Attorney, Agent, or Firm* — Lando & Anastasi, LLP

(57) ABSTRACT

In various embodiments, a dosimeter is employed to passively record a peak pressure (e.g., a peak blast pressure) and/or a maximum acceleration experienced by the dosimeter.

20 Claims, 11 Drawing Sheets

(51) Int. Cl.
*F41H 1/04* (2006.01)
*F42D 5/00* (2006.01)
*F42D 5/04* (2006.01)
*G01L 5/14* (2006.01)
*G01L 9/00* (2006.01)
*G01L 15/00* (2006.01)
*H01H 1/00* (2006.01)
*H01H 35/14* (2006.01)
*H01H 35/26* (2006.01)

(56) References Cited

U.S. PATENT DOCUMENTS

| | | |
|---|---|---|
| 4,040,172 A | 8/1977 | Kurtz et al. |
| 4,641,539 A | 2/1987 | Vilimek |
| 4,776,924 A | 10/1988 | Delapierre et al. |
| 4,827,414 A | 5/1989 | Christianson et al. |
| 4,837,548 A | 6/1989 | Lodini |
| 4,967,605 A | 11/1990 | Okada |
| 5,065,628 A | 11/1991 | Benecke |
| 5,357,807 A | 10/1994 | Guckel et al. |
| 5,834,646 A | 11/1998 | Kvisteroy et al. |
| 6,016,102 A | 1/2000 | Fortune et al. |
| 6,122,965 A | 9/2000 | Seidel et al. |
| 6,225,140 B1 | 5/2001 | Liu et al. |
| 6,263,739 B1 | 7/2001 | Seefried et al. |
| 6,308,575 B1 | 10/2001 | Yang et al. |
| 6,423,564 B1 | 7/2002 | Hulsing, II et al. |
| 6,526,832 B2 | 3/2003 | Landgraf et al. |
| 6,539,798 B1 | 4/2003 | Geiger et al. |
| 6,686,642 B2 | 2/2004 | Regan et al. |
| 6,700,174 B1 | 3/2004 | Miu et al. |
| 6,910,383 B2 | 6/2005 | Ou et al. |
| 7,043,995 B2 | 5/2006 | Mattmann |
| 7,122,396 B2 | 10/2006 | Nakamizo et al. |
| 7,223,624 B2 | 5/2007 | Wu et al. |
| 7,350,424 B2 | 4/2008 | Hjelt et al. |
| 2002/0053242 A1 | 5/2002 | Tai et al. |
| 2002/0185737 A1 | 12/2002 | Regan et al. |
| 2003/0201513 A1 | 10/2003 | Regan et al. |
| 2004/0118213 A1 | 6/2004 | Ou et al. |
| 2004/0183150 A1 | 9/2004 | Wang et al. |
| 2004/0237659 A1 | 12/2004 | Mattmann |
| 2005/0252308 A1* | 11/2005 | Hjelt et al. ............. 73/862.041 |
| 2006/0070444 A1 | 4/2006 | Nakamura |
| 2007/0261490 A1 | 11/2007 | Kai |
| 2008/0190207 A1 | 8/2008 | Yang |
| 2008/0202258 A1 | 8/2008 | Amin et al. |
| 2009/0152655 A1 | 6/2009 | Laming et al. |

OTHER PUBLICATIONS

"Unit VII: Explosive Blast" [online], Risk Management Series Slide Show for FEMA E155—Building Design for Homeland Security Course, U.S. Department of Homeland Security, Federal Emergency Management Agency, Jan. 2004, Retrieved from the Internet: <http://www.fema.gov/pdf/plan/prevent/rms/155/e155_day2.pdf>, 28 pages.

Baker "Sensors May Lead to Faster Treatment for Traumatic Brain Injuries," Defense.gov News, Jan. 14, 2008, 2 pages.

Bhattacharjee "Neuroscience: Shell Shock Revisited: Solving the Puzzle of Blast Trauma," Science, vol. 319, No. 5862, Jan. 25, 2008, pp. 406-408.

Francoeur, "Blast Strips Record Explosion Exposure," Military Applications, Jan. 2009, 2 pages.

Miles, "New Helmet Sensors to Measure Blast Impact," [online], American Forces Press Service, Jan. 7, 2008, [retrieved Apr. 26, 2010]. Retrieved from the Internet: <http://www.defense.gov/utility/printitem.aspx?print=http://www.defense.gov/news/newsarticle.aspx?id=48590>, 3 pages.

Sill, "Development of a Damped Piezoresistive MEMS High Shock Sensor," 78th Shock and Vibration Symposium, Nov. 4-8, 2007, 11 pages.

Souser, "A Helmet Patch to Measure Blasts," MIT Technology Review, Oct. 14, 2008, 4 pages.

Taber et al. "Blast-Related Traumatic Brain Injury: What Is Known?," J Neuropsychiatry Clin. Neurosci. No. 18, May 2006, pp. 141-145.

Taylor et al. "Simulation of Blast-Induced, Early-Time Intracranial Wave Physics leading to Traumatic Brain Injury" Sandia National Laboratories, United States Department of Energy's National Nuclear Security Administration, Contrac No. DE-AC04-94AL85000.2009, 13 pages.

Yang et al. "Investigation and simulation on the dynamic shock response performance of packaged high-g MEMS accelerometer versus the impurity concentration of the piezoresistor" Microelectronics Reliability, vol. 49, Issue 5, May 2009, pp. 510-516.

Zhang et al. "A Proposed Injury Threshold for Mild Traumatic Brain Injury", J. Biomech. Engr., vol. 126, No. 2, 2004, pp. 226-236.

Invitation to Pay Additional Fees and Partial International Search for PCT Application No. PCT/US2009/063436, Aug. 4, 2010, 5 pages.

International Search Report for PCT Application No. PCT/US2009/063436, Aug. 4, 2010, 5 pages.

Written Opinion for PCT Application No. PCT/US2009/063436, Aug. 4, 2010, 7 pages.

* cited by examiner

MEMS DOSIMETER

CROSS-REFERENCE TO RELATED APPLICATIONS

This application is a divisional of, and incorporates herein by reference in its entirety, U.S. patent application Ser. No. 12/613,446, which was filed on Nov. 5, 2009. U.S. patent application Ser. No. 12/613,446 claims priority to and the benefit of U.S. Provisional Patent Application No. 61/112,563, which was filed on Nov. 7, 2008 and is also incorporated herein by reference in its entirety.

TECHNICAL FIELD

In various embodiments, the present invention relates to a micro-electro-mechanical systems ("MEMS") dosimeter that passively records and reads out (e.g., electrically) a peak pressure (e.g., a peak blast pressure) and/or a maximum acceleration exposure.

BACKGROUND

Humans may experience high-pressure blasts in a variety of different contexts. For example, in military warfare, the increasing use of improvised explosive devices ("IEDs") has made traumatic brain injury ("TBI") a serious, hard-to-diagnose, and widespread injury. In addition to soldiers, however, other individuals who also work with explosives (e.g., construction workers, miners, etc.) may likewise experience a degree of high-pressure blasts, sometimes serious enough to cause TBI. Epidemiological studies are often needed to correlate blast exposure to the symptoms of brain injury. However, the data required to do these studies is typically lacking.

Portable blast monitors have been fielded to record blast exposure data and to correlate the exposure to the symptoms of brain injury. These blast monitors typically employ accelerometers and pressure sensors in combination with batteries, microprocessors, and digital memory for storing multiple event transients. These systems often provide key data linking blast exposure to TIM and permit treatments to be developed. However, the size and cost of these systems currently limits their use. As such, a need exists for an improved blast dosimeter.

In addition, there are a variety of situations in which it would be useful to record the maximum acceleration experienced by an object. For example, in shipping accidents, such as where packages are dropped, it would often be useful to know what the peak acceleration experienced by the packages was during their mishandling. Unfortunately, given the complexity, size, and cost of today's accelerometers, it is generally impractical to employ them for such a use. Accordingly, there is also a need for an improved dosimeter that measures a maximum acceleration experienced by an object.

SUMMARY OF THE INVENTION

In various embodiments, the present invention features a small, disposable MEMS dosimeter that accurately records and electrically reads out the peak blast pressure and/or acceleration experienced by the dosimeter, and that is low enough in cost to be universally deployed. In one embodiment, the MEMS dosimeter is a passive chip in the sense that no battery, other power source, microprocessor, or digital memory is present on the chip. Advantageously, in certain embodiments, the MEMS dosimeter may record a large volume of data that may be mined for studies of TBI versus peak blast pressure. The data may also be used in making immediate treatment decisions for soldiers exposed to IED or mortar blasts, and for other individuals exposed to similarly high-pressure blasts. In addition, the archived data may be used in making treatment decisions years later, if delayed symptoms arise.

In accordance with various embodiments of the invention, a plurality (e.g., an array) of fragile MEMS structures are formed on a chip (e.g., a silicon chip). Each structure is configured to break at a given pressure or acceleration. More specifically, for pressure recording, an array of membranes may be formed on (e.g., be integral with) a chip, with the burst pressure of each membrane determined by, for example, its size, shape, and/or material. For measuring peak acceleration, a set of cantilevers may be formed with small proof masses on a chip. Each cantilever may then be configured to break at a given acceleration level.

Advantages of the MEMS dosimeters described herein include a very low cost of manufacture, which makes the dosimeters disposable. In addition, each dosimeter can be extremely small an that it can be mounted almost anywhere. Moreover, because the MEMS dosimeters require no battery or other power source to operate, their shelf lives are essentially infinite.

From a commercial perspective, various embodiments of the MEMS dosimeters described herein may be used to document the high-pressure blasts experienced by soldiers, by construction workers, by miners, and/or by other individuals who work with explosives. The MEMS dosimeters may be applied, for example, to helmets, jackets, or other items with adhesives and be replaced as often as necessary. In addition, among other uses, the MEMS dosimeters may be employed in documenting shipping accidents, such as dropped packages. More particularly, the dosimeters may be employed as package and shipping monitors to measure peak acceleration from the mishandling of packages.

In general, in one aspect, embodiments of the invention feature a dosimeter for passively recording a pressure. The dosimeter includes a plurality of breakable structures (e.g., membranes) formed on a chip. At least one structure is breakable at a different pressure level than another structure for example, at least one structure is sized differently from another one of the structures (e.g., each structure may be sized differently from every other structure) or at least one structure is made from a different material than another one of the structures (e.g., each structure may be made from a different material than every other structure). In either case, breakage of a subset of the structures is indicative of the pressure experienced by the dosimeter.

In various embodiments, a resistor (e.g., a silicon or polysilicon resistor) is associated with each breakable structure. For example, each resistor may cross over its respective breakable structure or be embedded in its respective breakable structure. The resistors may also be wired in parallel, such that a later electrical measurement of the total resistance across the plurality of breakable structures (which will vary depending upon the number of broken (i.e., open-circuited) breakable structures) is indicative of the pressure experienced by the dosimeter.

Each breakable structure may be manufactured, at least in part, of silicon or polysilicon and may be configured to break at a particular pressure level. For example, one breakable structure may break at a pressure level of approximately 1 kPa, another breakable structure may break at a pressure level of approximately 1.4 MPa, and every other breakable structure may break at a particular pressure level in between those two extremes. The breakable structures may be substantially rectangular in shape, may have a re-entrant shape that concentrates stress in a pre-determined location, or may have another shape (e.g., circular).

In various embodiments, the chip includes pressure-equalization paths etched therein to equalize a pressure on each side of the breakable structures, but without altering their sensitivities to rapid pressure changes caused by blasts. When packaged, the dosimeter may include a lid that covers the plurality of breakable structures, and the lid may be perforated to allow a pressure (e.g., a blast pressure) to reach the array. However, a shield (e.g., a thin membrane) may be added to the lid to keep contaminants (e.g., dust, moisture, water, etc.) away from the plurality of breakable structures. In one embodiment, the chip is packaged without an internal power source.

In general, in another aspect, embodiments of the invention feature a dosimeter for passively recording an acceleration exposure. The dosimeter includes a plurality of breakable structures formed on a chip, which may be packaged without an internal power source. The breakable structures may be, for example, cantilevers. Optionally, the dosimeter may also include a proof mass coupled to at least one (e.g., every) cantilever. At least one breakable structure is breakable at a different level of acceleration than another structure—for example, at least one structure is sized differently from another one of the structures (e.g., each structure may be sized differently from every other structure) or at least one structure is made from a different material than another one of the structures (e.g., each structure may be made from a different material than every other structure). In either case, breakage of a subset of the structures is indicative of the acceleration experienced by the dosimeter. Each structure also includes an electrically conductive path constrained thereto that is open-circuited upon breakage of the structure.

In various embodiments, each electrically conductive path includes a resistor (e.g., a silicon or polysilicon resistor). Each resistor may cross over its respective breakable structure or be embedded in its respective breakable structure. Again, the resistors may be wired in parallel, such that a later electrical measurement of the total resistance across the plurality of breakable structures (which will vary depending upon the number of broken (i.e., open-circuited) breakable structures) is indicative of the acceleration level experienced by the dosimeter.

Each breakable structure may be manufactured, at least part, of silicon or polysilicon and be configured to break at a particular acceleration level. For example, one of the breakable structures may break at an acceleration of approximately g, another breakable structure may break at an acceleration of approximately 1000 g, and every other breakable structure may break at a particular level of acceleration in between those two extremes.

In general, in yet another aspect, embodiments of the invention feature a method for determining a pressure experienced by a chip, which, optionally, may be packaged without an internal power source. The method includes measuring a parameter associated with a plurality of interconnected, breakable structures formed on the chip, and determining the pressure experienced by the chip from the measured parameter. At least one of the breakable structures is breakable at a different pressure level than another breakable structure. In one embodiment, at least one of the structures will have been broken due to the pressure experienced thereby.

The measured parameter may be an electrical parameter, such as a resistance or a capacitance. As described above, the measured parameter changes upon breakage of each one of the breakable structures, which may each break at different pressure levels at or between approximately 1 kPa and approximately 1.4 MPa. In one embodiment, the method also includes equalizing a pressure on each side of at least one breakable structure without altering the breakable structure's sensitivity to rapid pressure changes caused by blasts.

In general, in still another aspect, embodiments of the invention feature a method for determining at acceleration experienced by a chip, which, optionally, may be packaged without an internal power source. The method includes measuring a parameter associated with a plurality of interconnected, breakable structures formed on the chip, and determining the acceleration experienced by the chip from the measured parameter. At least one of the breakable structures is breakable at a different level of acceleration than another structure, and each structure includes an electrically conductive path constrained thereto that is open-circuited upon breakage of the structure. In one embodiment, at least one of the breakable structures will have been broken due to the acceleration.

Again, the measured parameter may be an electrical parameter, such as a resistance or a capacitance. In addition, as described above, the measured parameter changes upon breakage of each one of the breakable structures, which may each break at different acceleration levels at or between approximately 2 g and approximately 1000 g.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

In various embodiments, the present invention features a MEMS dosimeter having a set of breakable structures, for example membranes or cantilevers that burst at well defined pressures or accelerations, respectively. This MEMS dosimeter need not include any batteries, other power sources, microprocessors, digital memories, or other active elements. Rather, in one embodiment, the MEMS dosimeter passively records a peak blast pressure or acceleration that it experiences, for example through a physical breakage of a select number of the membranes or cantilevers. As further described below, this peak blast pressure or acceleration may later be read out of the dosimeter (e.g., electrically read out) for various purposes (e.g., to rapidly measure and record the peak blast pressure experienced by a soldier, a construction worker, a miner, etc. to aid in the immediate treatment thereof, to conduct epidemiological studies, etc.).

Figure 1:
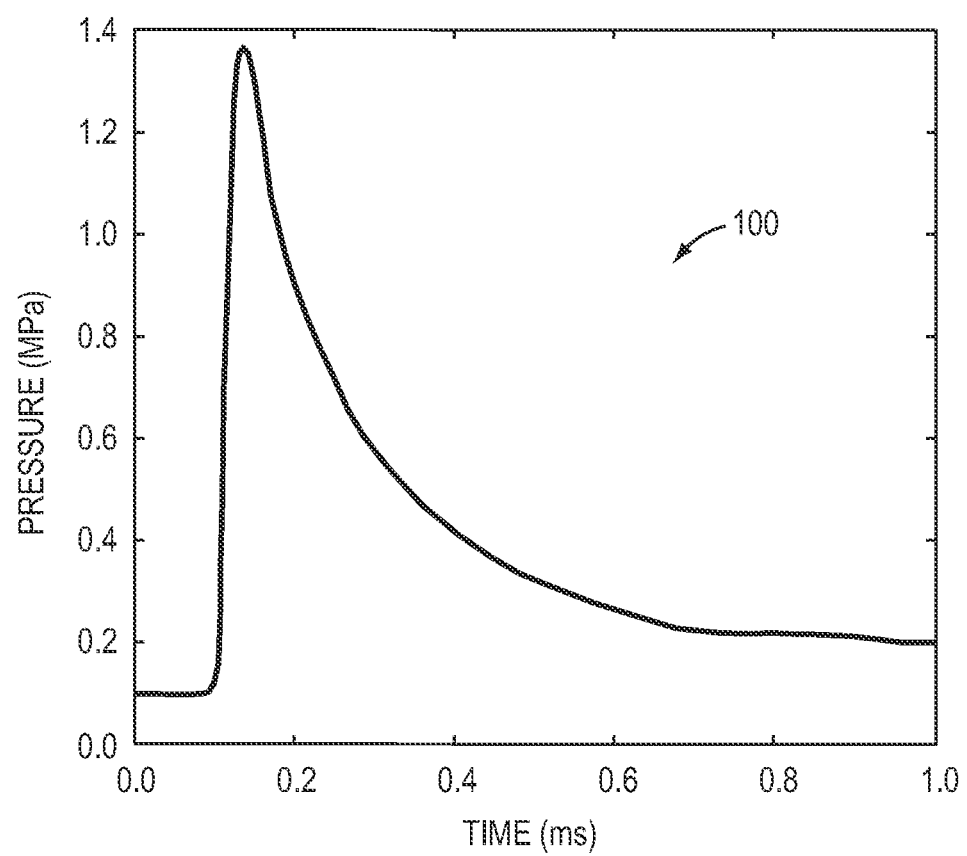
FIG. 1 is a graph illustrating blast transient pressure at approximately three meters from a typical IED.
Figure 2:
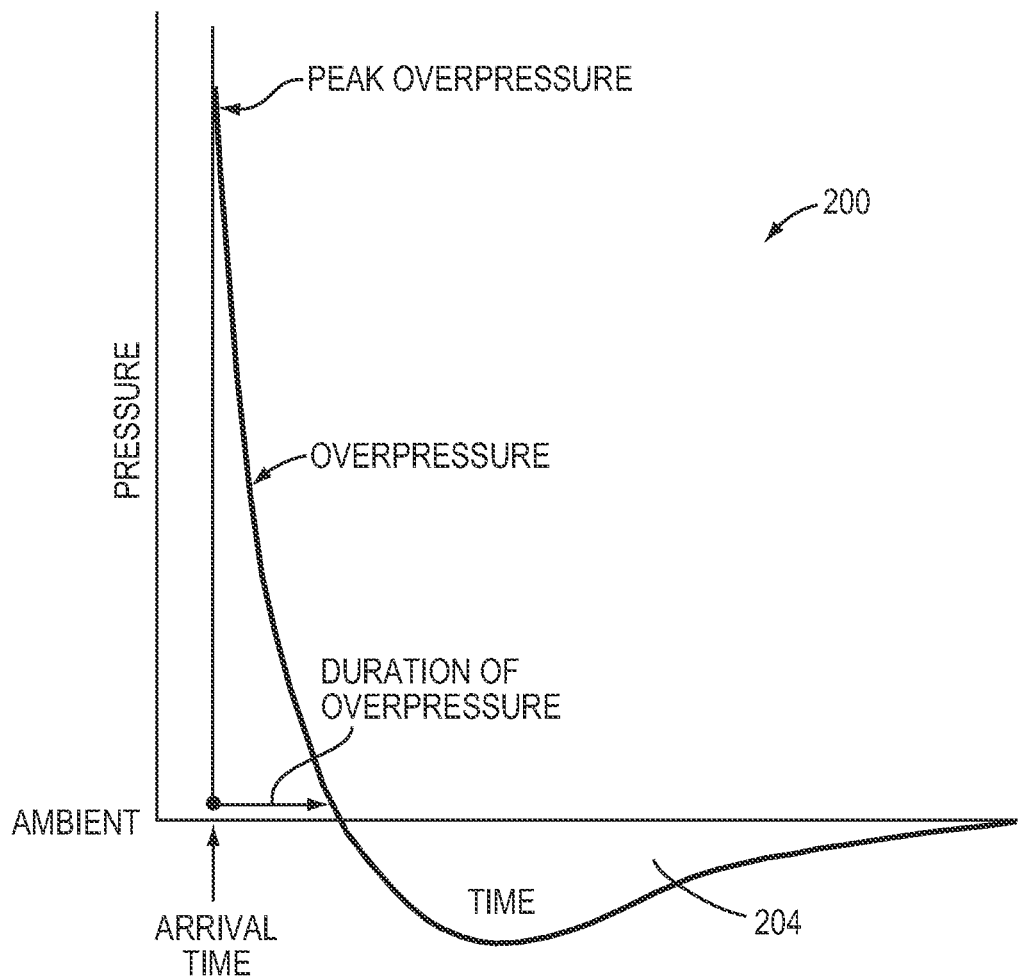
FIG. 2 is a graph illustrating an exemplary blast transient that has a negative pressure region.

FIG. 1 depicts a pressure waveform 100 from an LED at a range of approximately 3 meters, while FIG. 2 depicts a blast transient 200 having a negative pressure region 204. As shown in FIG. 1, the pressure waveform 100 has a peak pressure of approximately 1.4 MPa. A study performed at the Sandia National Laboratories modeled the human cranium using a detailed finite element analysis model. It showed that the peak stress induced in the human brain can be up to 4 times higher than an incident pressure wave, which implies either a focusing of the pressure wave or a resonance effect. The threshold for TBI damage is believed to be in the range of approximately 3-6 kPa, which is far below the pressure sustained by a soldier in proximity to an IED when it detonates.

Figure 3A:
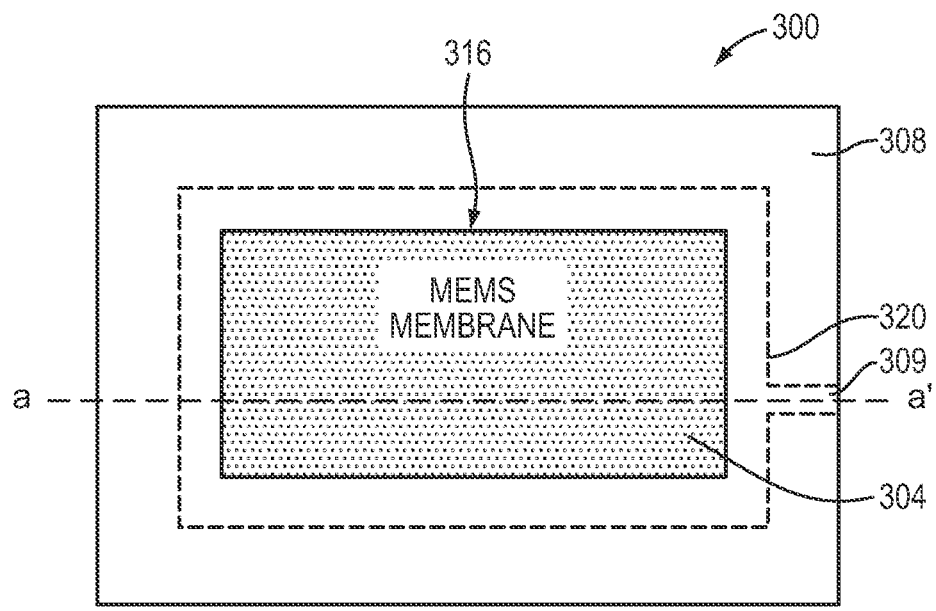
FIG. 3A is a schematic top view of a MEMS membrane device in accordance with one embodiment of the invention.
Figure 3B:
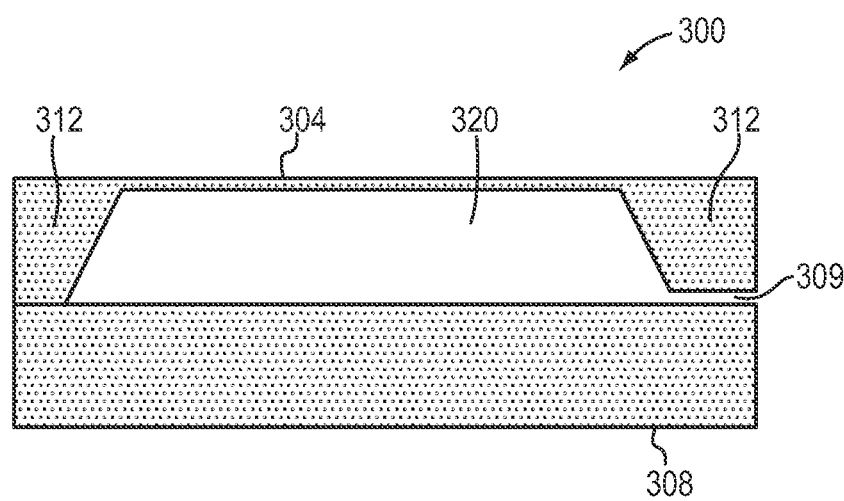
FIG. 3B is a schematic cross-sectional view of the MEMS membrane device of FIG. 3A along the line a-a'.

FIG. 3A depicts a top view of a MEMS membrane device 300 in accordance with one embodiment of the invention, while FIG. 3B depicts a cross-section of the membrane device 300 along the line a-a' of FIG. 3A. As illustrated, the MEMS membrane device 300 includes a membrane 304 coupled to a chip 308. In particular, a substrate 312 supporting the membrane 304 is coupled to the chip 308 and also suspends the membrane 304 over the chip 308. A cavity 320 is formed in the substrate 312 between the membrane 304 and the chip 308. In this way, a finite volume of air is contained below the membrane 304. As further described below, the MEMS membrane device 300 may be fabricated using standard MEMS technology to burst at a precisely defined pressure. For example, varying the size (e.g., length, width, and/or thickness) of the membrane 304 allows a wide range of blast pressures to be measured, as does employing different materials for the membrane 304.

Figure 4:
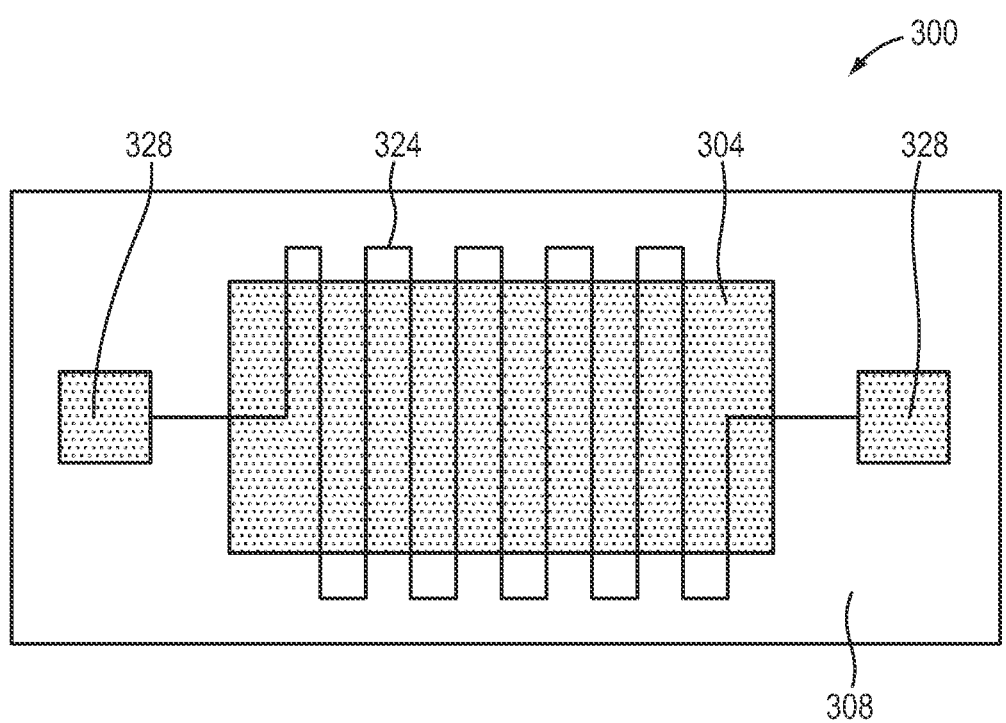
FIG. 4 schematically illustrates the MEMS membrane device of FIG. 3A with a resistor run to cross thereover.

As depicted in FIG. 4, a resistor 324 may cross over the membrane 304 by being patterned thereon. Alternatively, as described below, the resistor 324 may be embedded within the membrane 304. Either way, an open circuit electrical measurement may indicate that the membrane 304 has burst. The resistor 324 may include or consist essentially of silicon, polycrystalline silicon polysilicon), nichrome, or other resistive materials. For example, the resistor 324 may comprise ion-implanted polysilicon with a thin layer of silicon nitride (e.g., low-pressure chemical vapor deposited $Si_3N_4$) above and below the polysilicon layer. As illustrated, the ends of the resistor 324 electrically connect to con act pads 328. Alternatively, instead of a resistor 324, a capacitor may be connected between the contact pads 328. Again, in this way, an open circuit electrical measurement may indicate that the membrane 304 has burst.

A MEMS fabrication process may be used to manufacture the MEMS membrane device 300. Materials of construction well known to those skilled in the art of micromachining, and that may be used to manufacture the membrane 304, include, but are not limited to, silicon, polysilicon, Si—Ge alloys, Si—Ge—B alloys, $SiO_2$, $Si_3N_4$ and low stress SiN alloys, SiN, and AlN. In one embodiment, the membrane 304 is a sandwich of $Si_3N_4$/polysilicon/$Si_3N_4$. These materials have well controlled properties and give a precise and repeatable set of burst pressures. The polysilicon layer may also be used to form the resistor 324, white the $Si_3N_4$ layers form a tough passivation and etch stop for the membrane 304 formation. Another option is to use boron-diffused silicon, which forms a good membrane 304 etch stop layer.

Figure 5A:
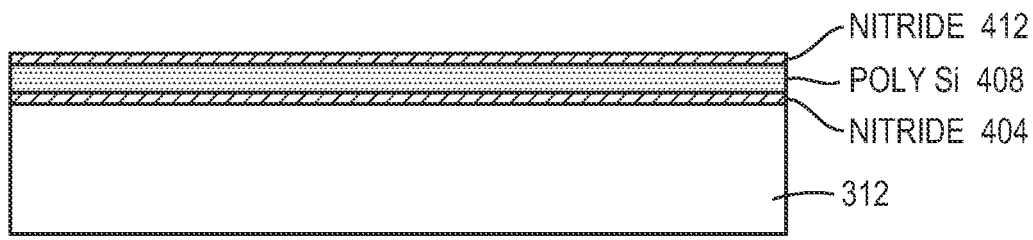
FIGS. 5A-5C schematically illustrate the steps in one embodiment of a method for fabricating a MEMS membrane device.
Figure 5B:
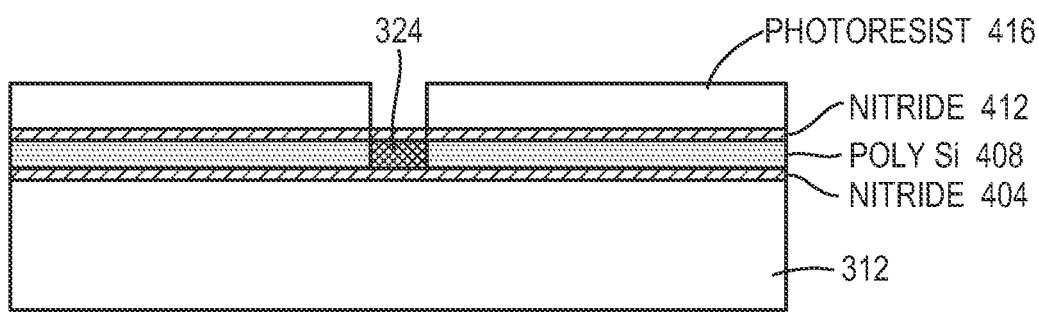
Figure 5C:
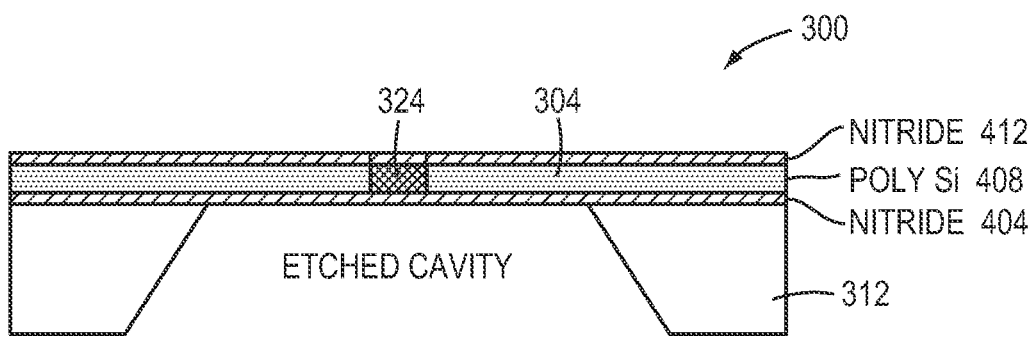

FIGS. 5A-5C schematically illustrate the steps in one exemplary embodiment of a method for fabricating the MEMS membrane device 300. Those skilled in the art will recognize that many other fabrication methods may alternatively be employed. As illustrated in FIG. 5A, a three layer stack of silicon nitride 404, polysilicon 408, and silicon nitride 412 may be formed on the membrane's substrate 312. Undoped polysilicon 408 has a very high resistivity (typically 10 GΩ/square), and can be considered an insulator to first order. As shown in FIG. 5B, ion implantation of selected regions of the polysilicon 408 through a photoresist mask 416 and through the top layer of silicon nitride 412 creates doped polysilicon resistor 324 paths. After a short anneal to activate the dopants, a highly resistive polysilicon membrane 304, with conductive resistor paths 324 embedded therein, is encapsulated within a high quality silicon nitride protective insulator 404, 412. Moreover, by adjusting the implant dose and implant mask areas, the resistivity of the resistor 324 paths can be controlled. Finally, as illustrated in FIG. 5C, the photoresist mask 416 may be removed and the substrate 312 may be etched to create the cavity 320 under the membrane 304.

Figure 6:
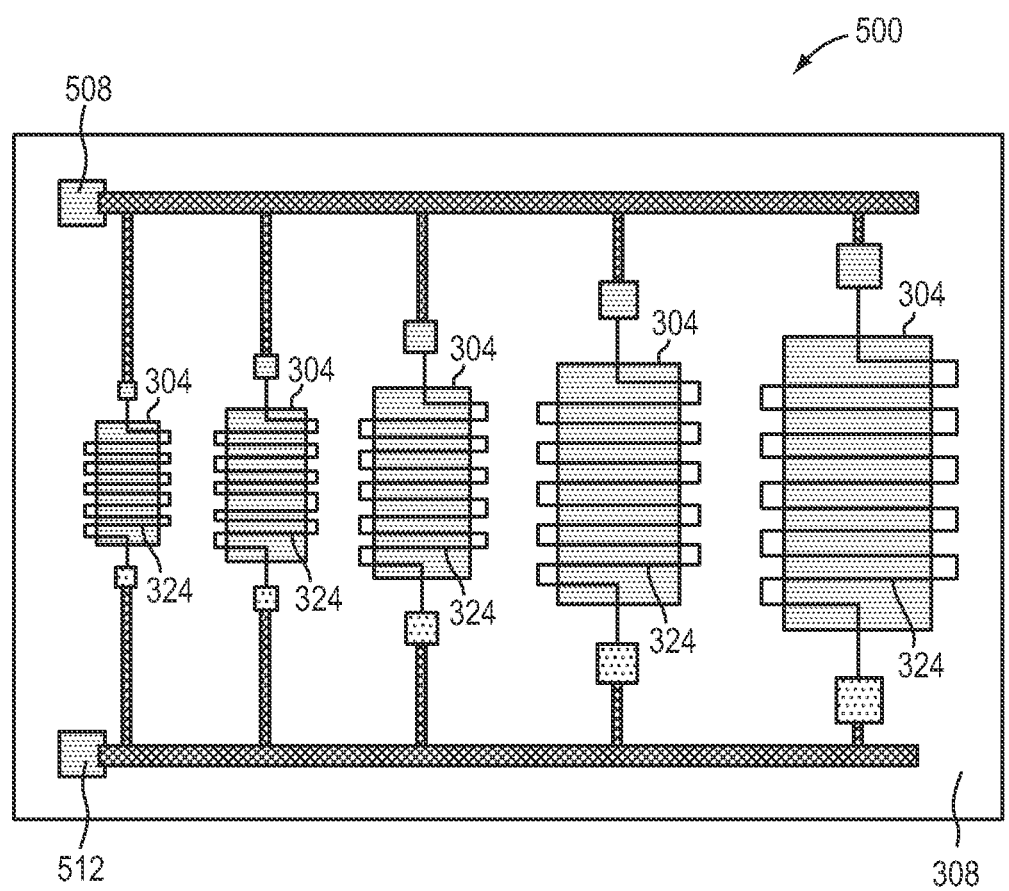
FIG. 6 schematically illustrates a MEMS dosimeter for passively recording a peak pressure in accordance with one embodiment of the invention.

In one embodiment, as illustrated in FIG. 6, a MEMS dosimeter 500 for passively recording a peak pressure (e.g., a peak blast pressure) may include a plurality (e.g., an array) of the MEMS membrane devices 300 formed on the chip 308 using, for example, the afore-described MEMS technology. At least one membrane 304 may be fabricated to have a different size (e.g., length, width, and/or thickness) than another membrane 304. For example, as illustrated in FIG. 6, each membrane 304 may be fabricated to have a different size and to therefore burst at a different pressure level, thereby allowing a wide range of blast pressures to be measured. Alternatively, each membrane 304 may be constructed from a different material than another membrane 304, such that each membrane 304 bursts at a different pressure level.

In one embodiment, as illustrated, the resistors 324 are wired in parallel. Alternatively, as mentioned previously, a plurality of capacitors may be employed instead of the resistors 324 and be wired in parallel. In either case, a later electrical measurement of the total impedance across the membrane 304 array (which will vary depending upon the number of broken (i.e., open-circuited) membranes 304) is indicative of the peak pressure experienced by the dosimeter 500. For example, to measure the resistance across the membrane 304 array, an external power source may be connected to contact pads 508, 512 of the dosimeter 500 to provide power thereto, and, for example, the leads of an external ohmmeter may then also be connected to the contact pads 508, 512. In one embodiment, the resistor 324 values are chosen to give an output resistance that varies strongly with peak pressure. Similarly, the external power source and a capacitance meter may likewise be employed to measure the capacitance across the membrane 304 array when capacitors are employed in place of the resistors 324.

The set of membrane 304 burst pressures may be selected to cover a range of pressures of interest. For example, one membrane 304 may break at a pressure level of approximately 1 kPa, another membrane 304 may break at a pressure level of approximately 1.4 MPa, and all other membranes 304 may break at a different pressure level therebetween. Alternatively, any other range of burst pressures may be chosen.

In one embodiment, as illustrated FIG. 6, each membrane 304 is substantially rectangular in shape. The burst pressure, $P_{burst}$, of a rectangular membrane is given by $$P_{burst} = \frac{\sigma_{max}}{\beta_1} \cdot \frac{t^2}{b^2}$$

where $\sigma_{max}$ is the maximum tensile strength of the membrane material, $\beta_1$ is a constant depending on the shape of the rectangle (approximately 0.5 for a 2:1 length/width ratio), t is the membrane thickness, and b is the short side length of the membrane.

Figure 7:
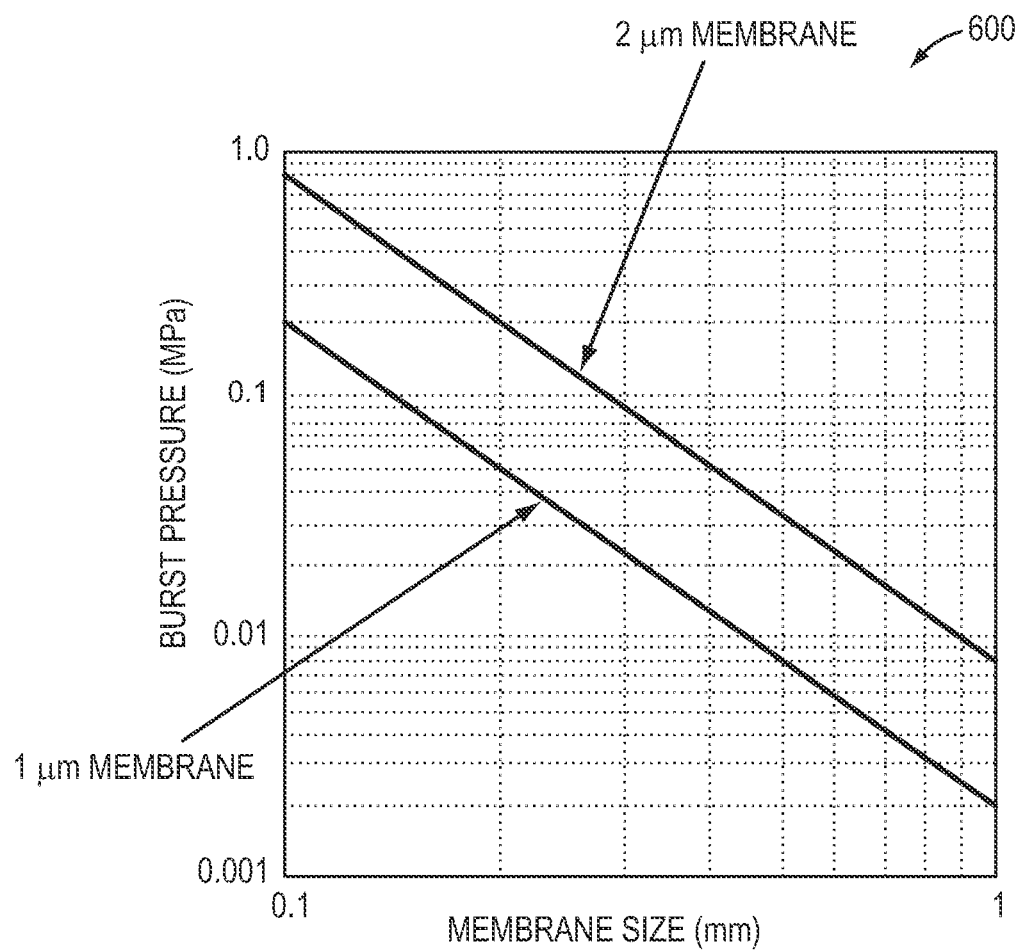
FIG. 7 is a graph illustrating burst pressure versus membrane size for two exemplary silicon membranes having thicknesses of one and two microns, respectively.

A plot 600 of burst pressure versus membrane 304 size is depicted in FIG. 7 for rectangular silicon membranes 304 of approximately 1 and 2 microns in thickness. The membrane 304 short side length is illustrated to range from approximately 0.1 mm to approximately 1 mm. As illustrated, these membranes 304 cover a range from approximately 0.02 atm to approximately 8 atm (i.e., approximately 160-206 dB SPL). A typical muzzle blast of a rifle is on the order of approximately 150 dB SPL, so membranes 304 of the size illustrated in FIG. 6 would be insensitive to normal battlefield sound levels. The sensed range may be adjusted by varying the size and shape of the membranes 304. For example, the thickness of each membrane 304, or portions of each membrane 304, may be varied by an additional photolithography and etch or selective deposition step to control the burst pressures.

Alternatively, the burst pressure from one membrane 304 to the next may be varied by manufacturing each membrane 304 from different materials. As one example, different materials having differing material properties that affect the breaking point of each membrane 304, such as different moduli of elasticity, fracture energies, strengths (e.g., compressive, fatigue, impact, and/or tensile strengths), fracture toughness, shear moduli, or the like, may be used in forming the membranes 304.

With reference back to FIG. 3A, the point of maximum stress 316 for t illustrated rectangular membrane 304 is at the middle of the tong edge of the membrane 304. In one embodiment, the resistor 324 (or capacitor) is run through this region of maximum stress 316 so that it will become open circuited when the membrane 304 bursts.

A threshold for TBI is in the range of approximately 3-6 kPa. Accordingly, in one embodiment, a lower limit of membrane 304 burst pressures is selected to be approximately 1 kPa. As illustrated FIG. 1, an IED exploding at a range of approximately 3 meters produces a peak pressure of approximately 1.4 MPa. Accordingly, 1.4 MN may be selected as the upper limit for membrane 304 burst pressures. The 3 decade range of peak pressures may then be covered logarithmically by choosing, for example, 3 burst pressures in each decade of pressure.

Rectangular membranes 304 are advantageous for several reasons. First, if silicon is employed in their manufacture, it can be anisotropically etched by various wet etches (e.g., KOH), thereby leaving very precise rectangular membranes 304 with smooth edges and well-defined burst pressures. Moreover, as just described, the peak stress point 316 of a rectangular membrane 324 is located iii the center of each long edge. Thus, placing a resistor 324 (or capacitor) to be broken at the center of those edges ensures that the resistor 324 (or capacitor) will be broken when the membrane 304 ruptures.

However, as will be readily understood by one of ordinary skill in the art, it may also be possible to vary the burst pressures of the membranes 304 by using shapes other than rectangular for the membranes 304. For example, round membranes 304 may be fabricated. In one embodiment, to fabricate the round membranes 304, a through-wafer inductively coupled plasma etch is used. However, this dry etching technique generally has a lower precision than the anisotropic wet etch that may be used to fabricate the rectangular membranes 304, i.e., control of the membrane 304 size using the plasma etch is somewhat less precise than using the wet etch. In addition, the cost per device using an expensive plasma etcher is substantially higher compared to wet etching.

Figure 8:
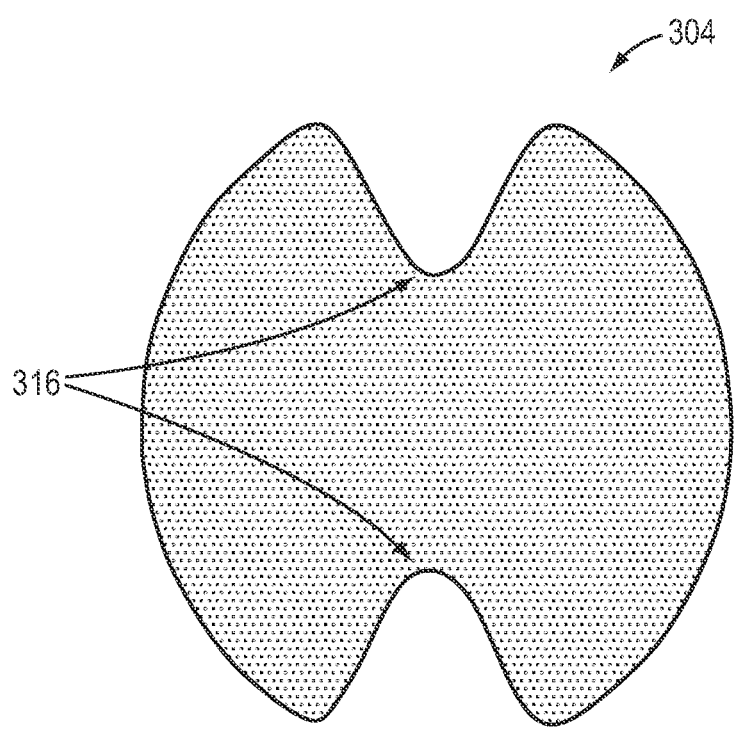
FIG. 8 schematically illustrates a MEMS membrane in accordance with another embodiment of the invention.

As another example, as illustrated in FIG. 8, a membrane 304 may have a re-entrant shape that concentrates stress in pre-determined locations 316. This re-entrant shape allows for a reduction in the size of the membranes 304 required to achieve a given burst pressure. Advantageously, this reduction in size can result in a cost savings, as it allows for more membranes 304 to be formed on a single chip 308. In one embodiment, the re-entrant-shaped membrane 304 is again fabricated via an inductively coupled plasma etch.

In one embodiment, as illustrated in FIG. 3B, each MEMS membrane device 300 contains a finite volume of air in the cavity 320 beneath its membrane 304. As the atmospheric pressure or the temperature of the dosimeter 500 changes, the pressure differential across a given membrane 304 will vary. These pressure changes, while small, could cause some variation in the response of the larger membranes 304. To prevent this, pressure-equalization paths 309 may be etched into the chip 308 of the dosimeter 500 to allow for a slow pressure-equalization (i.e., on the order of 0.1 to 10 minutes) on each side of the membranes 304, without altering the membranes' sensitivity to the rapid pressure changes caused by blasts. As illustrated in FIG. 3B, the pressure-equalization paths 309 may take the form of sub-micron deep etched channels on the side of the chip 308 opposite the membranes 304. These channels 309 may leak across the seal formed to the substrate 312.

Figure 9:
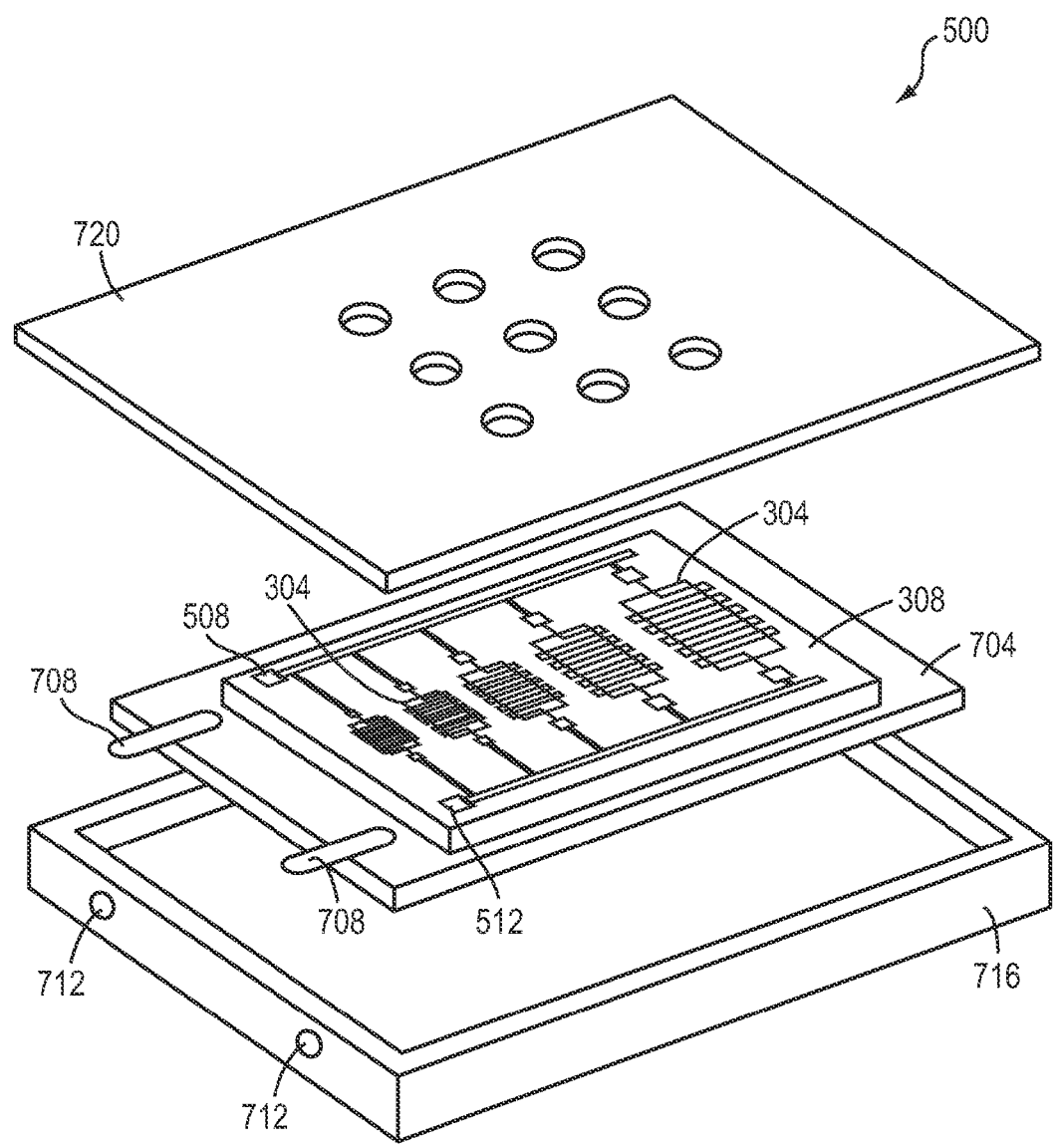
FIG. 9 is a schematic exploded view of a packaged blast dosimeter in accordance with one embodiment of the invention.

In one embodiment, the dosimeter 500 is packaged in a modified flat-pack, in a low cost leadless ceramic chip carrier, or in a plastic package with a lead frame. One embodiment of a packaged blast dosimeter 500 is depicted in FIG. 9. As illustrated, the dosimeter's chip 308 may be mounted on a board 704 (e.g., an alumina or ceramic board 704). In addition, the contact pads 508, 512 of the chip 308 may be wirebonded to leads or connectors 708, which may pass through holes 712 in a bottom portion 716 of the packaged dosimeter 500. A lid 720 for the dosimeter 500, which covers the array of membranes 304, may be perforated or be made of porous material to allow the blast pressure to reach the membranes 304.

Figure 10:
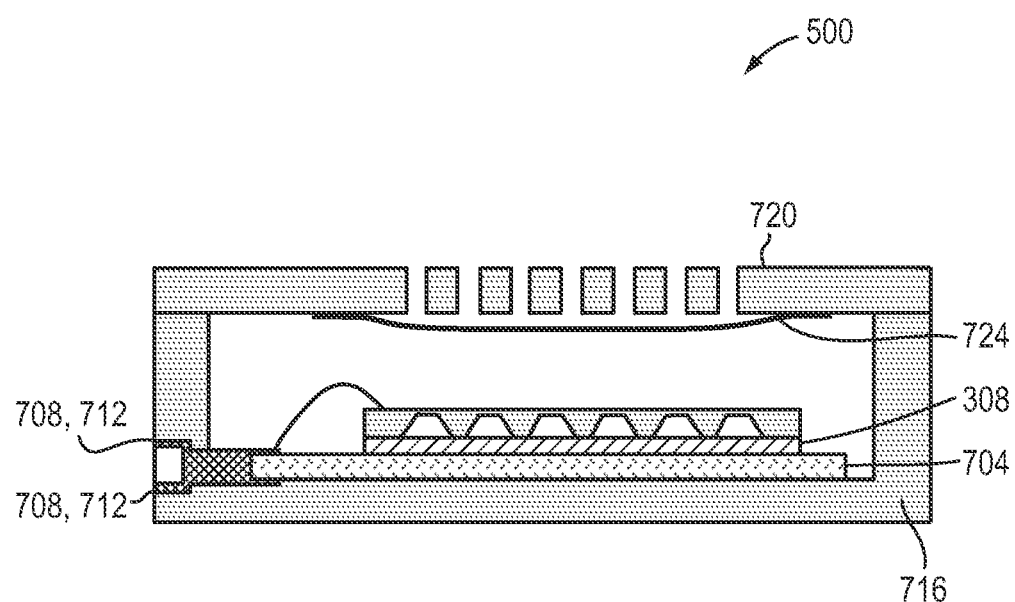
FIG. 10 is a cross-sectional view of the packaged blast dosimeter of FIG. 9.

FIG. 10 depicts a cross-sectional view of the packaged blast dosimeter 500 in accordance with one embodiment of the invention. As illustrated, a shield 724 (e.g., a thin membrane) may be coupled to the lid 720 to keep contaminants (e.g., dust, moisture, water, etc.) away from the chip 308. The shield 724 may be, for example, a water-repellant membrane, such as a Gore-Tex® membrane. In various embodiments, the package dosimeter 500 is adhesive mounted to a helmet (e.g., a soldiers' helmet) or to a hard hat (e.g., the hard hat of a construction worker or a miner), or is attached with an eyelet to a fabric surface.

Figure 11:
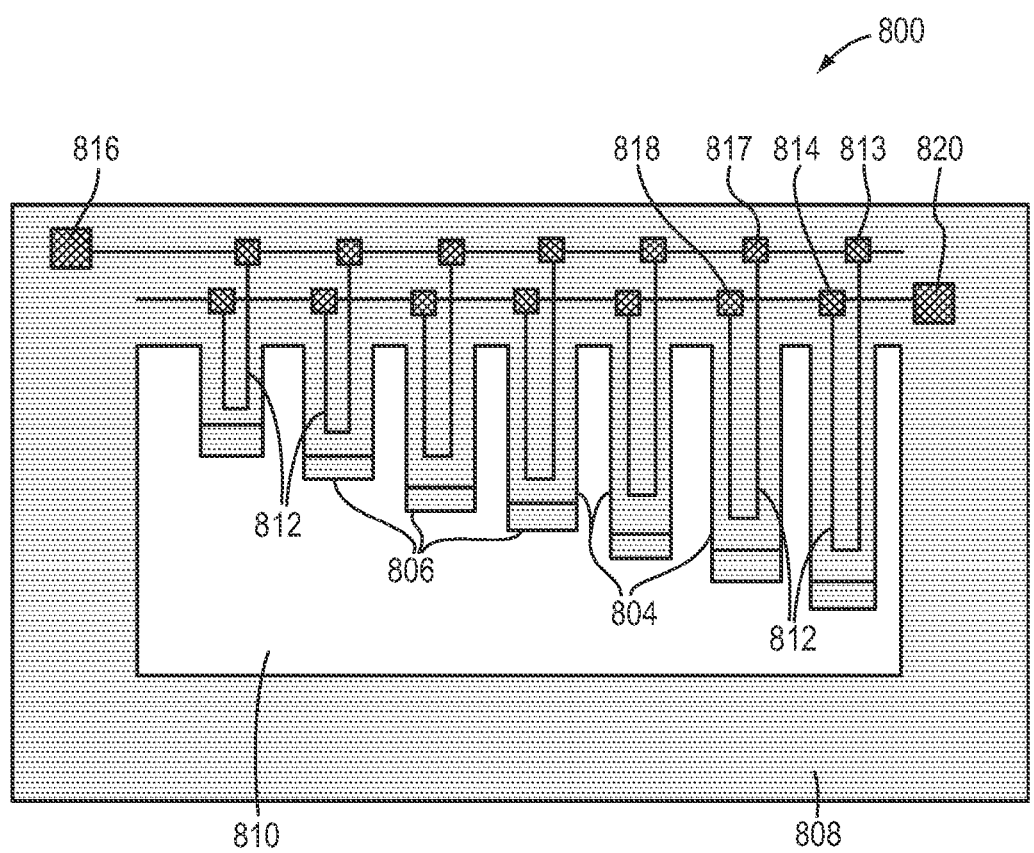
FIG. 11 schematically illustrates a MEMS dosimeter for passively recording a maximum acceleration exposure in accordance with one embodiment of the invention.

One of ordinary skill in the art will understand that a MEMS dosimeter for passively recording a maximum acceleration exposure may also be manufactured using the concepts described above. One such MEMS dosimeter 800 is depicted in FIG. 11. As illustrated, the exemplary dosimeter 800 includes a plurality (e.g., an array) of cantilevers 804 formed on a chip 808. More specifically, the chip 808 may have a cavity 810 defined (e.g., etched) therein, and each cantilever 804 may extend over that cavity 810. Each cantilever 804 may be constructed of any of the membrane 304 materials described above and may be configured to break at a different, given level of acceleration. For example, each cantilever 804 may be made from the same material (e.g., polysilicon), but be sized differently (e.g., in length, width, and/or thickness) so as to break at a different level of acceleration. Alternatively, as described above with respect to the membranes 304 each cantilever 804 may be made from a different material so as to break at a different level of acceleration. In one embodiment, one cantilever 804 in the array breaks at an acceleration level of approximately 2 g, another cantilever 804 in the array breaks at air acceleration level of approximately 1000 g, and every other cantilever 804 in the array breaks at an acceleration level therebetween. Optionally, a proof mass 806 may be coupled to one or more of the cantilevers 804 to change its breaking acceleration.

As illustrated, each cantilever 804 includes an electrically conductive path 812 constrained thereto that is open-circuited upon breakage of the cantilever 804. For example, the right-most cantilever 804 includes an electrically conductive path 812 between contact points 813 and 814, while the second right-most cantilever 804 includes an electrically conductive path 812 between contact points 817 and 818. Each electrically conductive path 812 is constrained its respective cantilever 804 in the sense that the electrically conductive path 812 does not contact another device, such as another cantilever 804, an overlying electrode, etc. In this way, frictional surfaces, which are generally detrimental to MEMS devices, are avoided between the electrically conductive paths 812 and other devices. Thus, the electrically conductive paths 812 do not rub against other devices, do not accidently weld thereto, and are less likely to corrode, become unstable, or introduce noise into the system.

Each electrically conductive path 812 may be a resistor of the type described above (e.g., a polysilicon resistor, a nichrome resistor, etc.) and may be open-circuited when its respective cantilever 804 breaks. The resistors 812 may be patterned to cross over their respective cantilevers 804 or be embedded therein. Again, capacitors may be employed in place; of the resistors 812 and, as shown, the resistors 812 (or capacitors) may be wired in parallel such that breakage of a single cantilever 804 (and, thus, of a single resistor 812 or capacitor) changes the read-out impedance of the dosimeter 800.

In greater detail, an electrical measurement of the total resistance or capacitance across the cantilever 804 array (which will vary depending upon the number of broken open-circuited) cantilevers 804) is indicative of the maximum acceleration experienced by the dosimeter 800. To measure the resistance across the cantilever 804 array, an external power source may be connected to contact pads 816, 820 of the dosimeter 800 to provide power thereto, and, for example, the leads of an external ohmmeter may then also be connected to the contact pads 816, 820. In one embodiment, the resistor 812 values are chosen to give an output resistance that varies strongly with the maximum acceleration experienced by the dosimeter 800. Similarly, the external power source and a capacitance meter may likewise be employed to measure the capacitance across the cantilever 804 array when capacitors are employed in place of the resistors 812.

Advantageously, as described herein, both the dosimeter 500 for passively recording a peak pressure and the dosimeter 800 for passively recording a maximum acceleration exposure may be packaged without an internal power source (i.e., the chips 308 and 808 may be unpowered), but may nevertheless still operate to measure and record the pressure or acceleration that they experience. By avoiding the use of internal power sources and other active elements (e.g., microprocessors and digital memories), the dosimeters 500, 800 may be manufactured very cheaply, may be extremely small, may be disposable, and may have essentially infinite shelf lives.

As described, the dosimeters 500, 800 may later be electrically interrogated to obtain the peak pressure or acceleration measurements that they store. Of course, those of ordinary skill in the art will understand that the dosimeters 500, 800 may also be interrogated in any number of other fashions. For example, the breakable structures (e.g., membranes 304 and cantilevers 804) may themselves be opaque, but be housed in a translucent or partially translucent package. In such a case, the dosimeters 500, 800 may be optically interrogated. For example, a light source may be placed on one side of the package and a device may be placed on the other side of the package to measure the intensity of the light transmitted therethrough (which will vary depending upon the number of broken membranes 304 or cantilevers 804). In such an embodiment, the intensity of the light is indicative of the peak pressure or acceleration experienced by the dosimeter 500, 800, and the resistors 324, 812 (or capacitors) need not be employed. Alternatively, a microscope or other magnifier may be employed to visually examine and record which membranes 304 or cantilevers 804 are broken. As such, the electrical interrogation described herein is non-limiting.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A dosimeter for passively recording an acceleration exposure, comprising:
   a plurality of breakable structures formed on a chip, at least one structure being breakable at a different level of acceleration than another structure, at least one of the breakable structures sized differently from another one of the breakable structures and each structure comprising an electrically conductive path constrained thereto that is open-circuited upon breakage of the structure, the electrically conductive paths wired in parallel such that a measurement of a total resistance across the plurality of breakable structures is indicative of an acceleration level experienced by the dosimeter, each electrically conductive path including a first contact point and a second contact point, and wherein breakage of a subset of the structures is indicative of the acceleration experienced by the dosimeter; and a pair of contact pads formed on the chip and connected to the electrically conductive path of each structure through the first contact point and the second contact point such that a first contact pad of the pair of contact pads is connected to the first contact point and a second contact pad of the pair of contact pads is connected to the second contact point.

2. The dosimeter of claim 1, wherein at least one of the breakable structures is a cantilever.

3. The dosimeter of claim 2 further comprising a proof mass coupled to the cantilever.

4. The dosimeter of claim 1, wherein at least one of the breakable structures comprises a material different from another one of the breakable structures.

5. The dosimeter of claim 1, wherein each electrically conductive path comprises a resistor.

6. The dosimeter of claim 5, wherein each resistor crosses over its respective breakable structure.

7. The dosimeter of claim 5, wherein each resistor is embedded in its respective breakable structure.

8. The dosimeter of claim 5, wherein each resistor comprises at least one of silicon or polysilicon.

9. The dosimeter of claim 1 wherein each breakable structure comprises at least one of silicon or polysilicon.

10. The dosimeter of claim 1, wherein one of the breakable structures breaks at an acceleration of approximately 2 g.

11. The dosimeter of claim 1, wherein one of the breakable structures breaks at an acceleration of approximately 1000 g.

12. The dosimeter of claim 1, wherein each breakable structure breaks at an acceleration between approximately 2 g and 1000 g.

13. The dosimeter of claim 1, wherein the chip is packaged without an internal power source.

14. A method for determining an acceleration, comprising:

measuring at least one of a total resistance and a total capacitance associated with a plurality of interconnected, breakable structures formed on a chip using a first contact pad and a second contact pad, at least one structure being breakable at a different level of acceleration than another structure, at least one of the breakable structures sized differently from another one of the breakable structures and each structure comprising an electrically conductive path constrained thereto that is open-circuited upon breakage of the structure and having a first contact point connected to the first contact pad and a second contact point connected to the second contact pad, and at least one of the structures and the respective electrically conductive path having been broken due to the acceleration; and determining the acceleration experienced by the chip from the at least one measured total resistance and total capacitance.

15. The method of claim 14, wherein the at least one measured parameter total resistance and total capacitance changes upon breakage of each one of the breakable structures.

16. The method of claim 14, wherein one of the breakable structures breaks at an acceleration of approximately 2 g.

17. The method of claim 14, wherein one of the breakable structures breaks at an acceleration of approximately 1000 g.

18. The method of claim 14, wherein each breakable structure breaks at an acceleration between approximately 2 g and 1000 g.

19. The method of claim 14, wherein the chip is packaged without an internal power source.

20. A dosimeter for passively recording an acceleration exposure, comprising:

a chip having a cavity defined therein;

an array of cantilevers formed on the chip, such that at least a portion of each cantilever extends over the cavity of the chip, each cantilever of the array of cantilevers being sized differently and breakable at a different level of acceleration than every other cantilever and each cantilever comprising an electrically conductive path between a pair of contact points that is open-circuited upon breakage of the cantilever, the electrically conductive paths wired in parallel such that a measurement of a total resistance across the array of cantilevers is indicative of an acceleration level experienced by the dosimeter;

a first contact pad formed on the chip and connected to a first contact point of each of the pairs of contact points; and a second contact pad formed on the chip and connected to a second contact point of each of the pairs of contact points.

* * * * *

UNITED STATES PATENT AND TRADEMARK OFFICE
CERTIFICATE OF CORRECTION

| | | |
|---|---|---|
| PATENT NO. | : 9,465,047 B2 | Page 1 of 1 |
| APPLICATION NO. | : 13/563245 | |
| DATED | : October 11, 2016 | |
| INVENTOR(S) | : Jonathan J. Bernstein | |

It is certified that error appears in the above-identified patent and that said Letters Patent is hereby corrected as shown below:

In the Specification

Column 2, line 23, replace "an" with --so--

Column 5, line 67, insert --(i.e.,-- between "silicon" and "polysilicon"

Column 7, line 61, replace "t" with --the--

Column 7, line 62, replace "tong" with --long--

Column 8, line 15, replace "iii" with --in--

Column 9, line 13, replace "package" with --packaged--

Colum 9, line 50, insert --to-- between "constrained" and "its"

Column 9, line 65, replace "irr" with --in--

In the Claims

Column 12, line 18, remove the word "parameter"

Signed and Sealed this
Sixth Day of December, 2016

Michelle K. Lee
*Director of the United States Patent and Trademark Office*